US012185997B2

(12) United States Patent
McClintock et al.

(10) Patent No.: US 12,185,997 B2
(45) Date of Patent: Jan. 7, 2025

(54) PEDICLE FIXATION SYSTEM

(71) Applicant: K2M, Inc., Leesburg, VA (US)

(72) Inventors: Larry E. McClintock, Gore, VA (US); Jason Noel Gantick, Purcellville, VA (US); Peter Newton, La Jolla, CA (US)

(73) Assignee: K2M, Inc., Leesburg, VA (US)

( * ) Notice: Subject to any disclaimer, the term of this patent is extended or adjusted under 35 U.S.C. 154(b) by 308 days.

(21) Appl. No.: 17/634,817

(22) PCT Filed: Aug. 14, 2020

(86) PCT No.: PCT/US2020/046370
§ 371 (c)(1),
(2) Date: Feb. 11, 2022

(87) PCT Pub. No.: WO2021/034664
PCT Pub. Date: Feb. 25, 2021

(65) Prior Publication Data
US 2022/0323128 A1 Oct. 13, 2022

Related U.S. Application Data

(60) Provisional application No. 62/886,431, filed on Aug. 14, 2019.

(51) Int. Cl.
*A61B 17/70* (2006.01)
*A61B 17/84* (2006.01)
*A61B 17/88* (2006.01)

(52) U.S. Cl.
CPC ........ *A61B 17/846* (2013.01); *A61B 17/7002* (2013.01); *A61B 17/7032* (2013.01)

(58) Field of Classification Search
CPC .............. A61B 17/846; A61B 17/7002; A61B 17/7032; A61B 17/7043; A61B 17/58;
(Continued)

(56) References Cited

U.S. PATENT DOCUMENTS

| 5,735,851 A | 4/1998 | Errico et al. |
| 5,800,435 A | 9/1998 | Errico et al. |

(Continued)

FOREIGN PATENT DOCUMENTS

| EP | 1254639 A1 | 11/2002 |
| JP | 2001252283 A | 9/2001 |

(Continued)

OTHER PUBLICATIONS

Partial European Search Report issued in Appln. No. 20854290.2 dated Oct. 4, 2022 (5 pages).

(Continued)

*Primary Examiner* — Eduardo C Robert
*Assistant Examiner* — David C Comstock
(74) *Attorney, Agent, or Firm* — Lerner David LLP

(57) ABSTRACT

A pedicle fixation system (10) may include a first fastener (12) and a second fastener (14). The first fastener (12) may include a first shank (40) extending along a first fastener axis (41) and a channel (52) extending along a skew axis (51). The skew axis (51) may be transverse to the first fastener axis (41) and the channel (52) may have a channel diameter perpendicular to the skew axis (51). The second fastener (14) may extend through the channel (52) and include a second shank (60) extending along a second fastener axis (63). At least a distal part of the second shank (60) may have a second fastener diameter perpendicular to the second fastener axis (63). The second fastener diameter may be smaller than the channel diameter.

17 Claims, 8 Drawing Sheets

(58) Field of Classification Search
CPC ... A61B 17/70; A61B 17/7035; A61B 17/704; A61B 17/7049; A61B 17/86; A61B 17/8625
USPC ....... 606/246, 266, 279, 286, 287, 300, 304, 606/305, 306, 307, 308, 310, 314, 319, 606/323, 328, 329
See application file for complete search history.

(56) References Cited

U.S. PATENT DOCUMENTS

| | | | |
|---|---|---|---|
| 6,074,391 | A | 6/2000 | Metz-Stavenhagen et al. |
| 6,261,287 | B1 | 7/2001 | Metz-Stavenhagen |
| 6,280,442 | B1 | 8/2001 | Barker et al. |
| 6,488,681 | B2 | 12/2002 | Martin et al. |
| 6,736,820 | B2 | 5/2004 | Biedermann et al. |
| 6,974,460 | B2 | 12/2005 | Carbone et al. |
| 7,537,664 | B2 | 5/2009 | O'Neill et al. |
| 7,947,065 | B2 | 5/2011 | Hammill, Sr. et al. |
| 8,147,861 | B2 | 4/2012 | Jones et al. |
| 8,192,470 | B2 | 6/2012 | Biedermann et al. |
| 8,350,186 | B2 | 1/2013 | Jones et al. |
| 8,435,272 | B2 | 5/2013 | Dougherty et al. |
| 8,728,387 | B2 | 5/2014 | Jones et al. |
| 8,992,703 | B2 | 3/2015 | O'Neill et al. |
| 9,044,273 | B2 | 6/2015 | Richelsoph et al. |
| 9,060,808 | B2 | 6/2015 | Overes et al. |
| 9,084,646 | B2 | 7/2015 | Sevrain |
| 9,119,674 | B2 | 9/2015 | Matthis et al. |
| 9,135,374 | B2 | 9/2015 | Jones et al. |
| 9,149,316 | B2 * | 10/2015 | Appenzeller ...... A61B 17/8685 |
| 9,180,010 | B2 | 11/2015 | Dong et al. |
| 9,204,911 | B2 | 12/2015 | Overes et al. |
| 9,289,220 | B2 | 3/2016 | Wolfe et al. |
| 9,456,901 | B2 | 10/2016 | Jones et al. |
| 9,649,133 | B2 * | 5/2017 | Strnad ................ A61B 17/8685 |
| 2003/0149487 | A1 | 8/2003 | Doubler et al. |
| 2005/0059972 | A1 * | 3/2005 | Biscup ............... A61B 17/7061 606/907 |
| 2005/0209698 | A1 | 9/2005 | Gordon et al. |
| 2006/0036253 | A1 * | 2/2006 | Leroux .................. A61B 17/70 623/23.57 |
| 2006/0147332 | A1 | 7/2006 | Jones et al. |
| 2008/0086131 | A1 * | 4/2008 | Daly .................. A61B 17/7044 606/103 |
| 2009/0093851 | A1 | 4/2009 | Osman |
| 2010/0030273 | A1 | 2/2010 | Mitchell et al. |
| 2010/0145397 | A1 | 6/2010 | Overes et al. |
| 2010/0312280 | A1 * | 12/2010 | Overes .................. A61B 17/68 606/279 |
| 2012/0046698 | A1 | 2/2012 | Kolb et al. |
| 2012/0197254 | A1 * | 8/2012 | Wolfe ................ A61B 17/1775 606/62 |
| 2013/0274818 | A1 * | 10/2013 | Goshayeshgar ..... A61B 17/864 606/310 |
| 2016/0128732 | A1 | 5/2016 | Strnad et al. |
| 2017/0020572 | A1 | 1/2017 | Hynes et al. |
| 2017/0105768 | A1 | 4/2017 | Pinkie |
| 2018/0214187 | A1 | 8/2018 | Shoshtaev et al. |
| 2021/0251662 | A1 * | 8/2021 | Lee .................... A61B 17/7037 |
| 2021/0315620 | A1 * | 10/2021 | Fessler .................. A61B 17/70 |

FOREIGN PATENT DOCUMENTS

| | | |
|---|---|---|
| JP | 3383257 B2 | 3/2003 |
| WO | 2011014135 A2 | 2/2011 |

OTHER PUBLICATIONS

Supplemental European Search Report issued in Appln. No. 20854290.2 dated Sep. 23, 2022. (4 pages).

International Search Report for Application No. PCT/US2020/046370 mailed Oct. 26, 2020, 1 page.

* cited by examiner

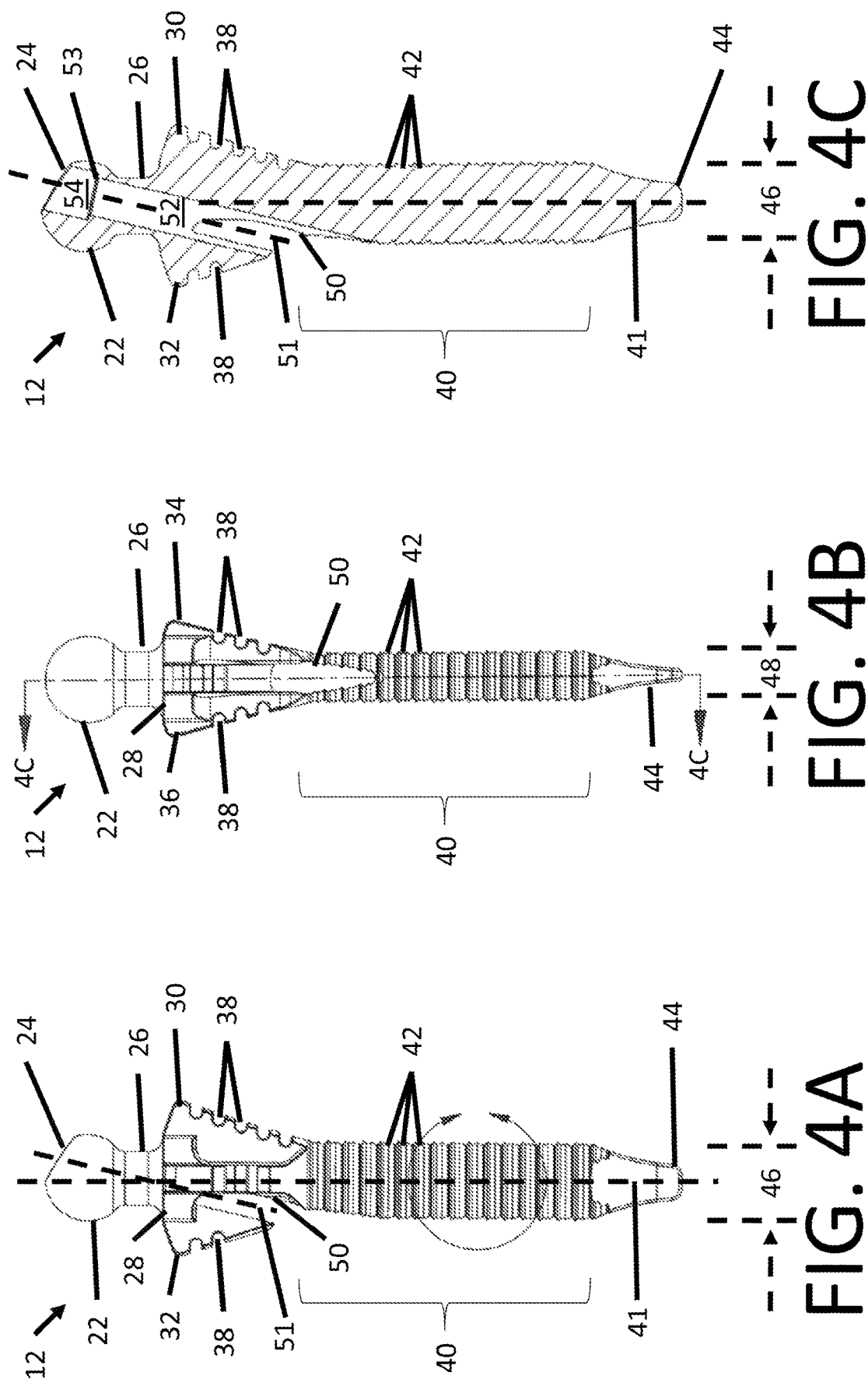

PEDICLE FIXATION SYSTEM

CROSS REFERENCE TO RELATED APPLICATIONS

The present application is a national phase entry under 35 U.S.C. § 371 of International Application No. PCT/US2020/046370, filed Aug. 14, 2020, which claims priority from U.S. Provisional Patent Application No. 62/886,431, filed Aug. 14, 2019, all of which are incorporated herein by reference.

BACKGROUND

The spine or spinal column is a complex system of bones and connective tissues that provide support for the human body and protection for the spinal cord and nerves. The adult spine is comprised of an upper portion and a lower portion. The upper portion contains twenty-four discrete vertebrae, which are subdivided into three areas including seven cervical vertebrae, twelve thoracic vertebrae, and five lumbar vertebrae. The lower portion is comprised of the sacral and coccygeal bones. The cylindrical shaped bones, called vertebrae or vertebral bodies, progressively increase in size from the upper portion downwards to the lower portion.

An intervertebral disc, along with two posterior facet joints, cushion and dampen the various translational and rotational forces exerted upon the spinal column. The intervertebral disc is essentially a spacer located between two adjacent vertebral bodies, while the facets provide stability to the posterior portion of adjacent vertebrae. The spinal cord is housed in a canal formed in a posterior aspect of the vertebral bodies, and is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which may restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function and range of mobility. These conditions and their treatments can be further complicated if the patient is suffering from osteoporosis, or bone tissue thinning and loss of bone density.

Spinal fixation apparatuses are widely employed in surgical processes for correcting spinal injuries and diseases that require the imposition and/or maintenance of corrective forces on the spine in order to return it to its normal condition. In order to facilitate stabilizing the spine and keeping the interbody in position, other implants are commonly employed, such as bone screws and rods. One type of spinal construct may include, for example, one or more spinal rods that can be placed generally parallel to the spine with fixation devices (e.g., hooks, screws, or plates) interconnected between the spinal rods at selected portions of the spine. The spinal rods can be connected to each other via cross-connecting members to provide a more rigid support and alignment system.

Most common among the aforementioned fixation devices are the use of pedicle screws inserted into two or more vertebrae. A rod is then placed within or coupled to the heads of the screws, or is placed within a connecting device that links the rod and a screw head, and the connections are tightened. In this way, a rigid supporting structure is fixed to the vertebrae, with the rod providing the support that maintains and/or promotes correction of the vertebral malformation or injury.

Usually, the surgeon attaches the spinal fixation devices to the spine in the appropriate anatomical positions and then attaches the spinal rod to the fixation devices. In conjunction with assembling the rod construct, the surgeon manipulates the spinal column and/or individual vertebrae to provide the desired treatment for the spinal defect. Subsequently, the spinal rod and fixation devices are locked in a desired arrangement.

Known methods and devices for certain spinal fixation methods may require a physician to screw a large total number of fixation devices into the spine before the spinal column can be manipulated and before the rod can be positioned and locked into place. Screwing in the necessary fixation devices may therefore be time consuming and fatiguing to the physician, and as such may contribute to a risk of various negative outcomes. Further, known spinal screws have a potential to turn within the bone, resulting in loosening over time. This is especially true in instances where bone quality is less than optimal. Accordingly, methods and devices for relatively fast and secure spinal fixation requiring less physical effort from the surgeon would be beneficial.

BRIEF SUMMARY

The present disclosure relates to a fixation system for retaining a spinal correction rod. The fixation system may include a first fastener, a second fastener, and a coupling element for retaining the correction rod to the first fastener. The first fastener and second fastener may be mutually configured such that the second fastener may provide a secondary fastening of the first fastener to bone. Either or both of the first fastener and the second fastener may include rings or a texture along their respective shanks to promote retention in bone. Further, either or both of the first fastener and second fastener may be an impactable fastener, such as a nail.

In accordance with an aspect of the present disclosure, an impactable fixation system for retaining a spinal correction rod may include a first nail having a first head and a coupling device capable of pivotally coupling to the first head and retaining the spinal correction rod. The system may further include a second nail, and the first nail may include a channel through which the second nail is receivable. The channel may extend distally from an opening in the first head in a direction transverse to a first shank of the first nail. The channel may further include a cavity located at the opening in the first head and having greater diameter than the rest of the channel. The second nail may have a second head of greater diameter than a second shank such that the second head may seat against a shelf defined by a distal end of the cavity. Either or both of the first shank and the second shank may have textured surfaces provided by a series of rings extending there along. The first nail may further include shoulders extending outward from a platform distal of the first head, and the shoulders may have notches to promote engagement with a bone. Further, the first shank may have an oblong or oval cross-sectional shape to provide additional surface area for engagement with bone.

A method of using the fixation system may include driving the first nail into a pedicle of a vertebra in an anterior direction, or in a direction perpendicular to a posterior surface of the pedicle. The first nail may be oriented such that a width of the oval cross-sectional shape of the first shank and a longer pair of the shoulders are neuraxially aligned, or oriented with a relatively long dimension of the pedicle. The second nail may be driven into the pedicle through the channel in the first nail until the second head seats against the shelf to provide a secondary fastening of the first nail to the pedicle. The channel, and therefore the second nail upon driving into the pedicle, may be oriented caudally, toward the feet of the patient, or in a direction with a greater neuraxial component than the direction in which the first nail was driven. Either or both of the first and second nail may be driven with a hammer, such as with an externally powered impact hammer. The coupling element may be pivotally coupled to the first head. Other fixation systems may be attached to other vertebrae and the vertebrae may be manipulated into an intended alignment. A spinal correction rod may be reduced onto and fixed to the coupling elements to correct the curvature of the spine.

In another aspect, a pedicle fixation system may include a first fastener and a second fastener. The first fastener may include a first shank extending along a first fastener axis and a channel extending along a skew axis. The skew axis may be transverse to the first axis and the channel may have a channel diameter perpendicular to the skew axis. The second fastener may extend through the channel and include a second shank extending along a second fastener axis. At least a distal part of the second shank may have a second fastener diameter perpendicular to the second fastener axis. The second fastener diameter may be smaller than the channel diameter.

At least part of the channel may have a dimension that is smaller than a dimension of a second head included by the second fastener. The first fastener may be a nail. At least part of the first shank may include a textured surface defined by a series of rings extending along the shank. The first fastener may include a generally spherical first head. The channel may extend from an opening in the first head. The fixation system may include a coupling element that includes a pocket shaped to pivotally couple to the first head. A majority of the first shank may have a generally oval shaped axial cross section relative to the first axis. The generally oval shaped cross section may have a width to thickness ratio of at least 4:3.

In another aspect, a pedicle fixation system may include a first nail and a coupling element. The first nail may include a generally spherical first head at a proximal end and a first shank extending distally from the first head along a first axis. A coupling element including a track shaped to couple to a rod and a pocket shaped to pivotally couple to the first head.

The first nail may further include a channel extending along a skew axis, and the skew axis may be transverse to the first axis. The channel may extend from an opening in the first head. The channel may extend into a shoulder that extends radially outward from the fastener relative to the first axis. The second fastener may be at least partially receivable through the channel. The second fastener may be a nail.

In another aspect, a method of installing a pedicle fixation system may include inserting a first fastener into a vertebral body in a first direction, and inserting in a second fastener in a second direction transverse to the first direction through the first fastener and into the vertebral body. The second fastener may be inserted such that the second fastener secondarily fastens the first fastener into the vertebral body.

The inserting of the first fastener may include hammering the first fastener into the vertebral body. The inserting of the second fastener may include hammering the second fastener into the vertebral body. The method may include hammering a third fastener into a second vertebral body, attaching coupling elements to the first and third fasteners; and inserting a rod through the coupling elements such that the first and third fasteners are coupled to the rod. The method may include coupling a first head included by the first fastener to a rod. The method may include pivotally attaching a coupling element to a first head included by the first fastener. The method may include coupling the coupling element to a spinal correction rod. The first direction may be generally anterior, and the second direction may have a greater neuraxial component than the first direction.

BRIEF DESCRIPTION OF THE DRAWINGS

FIG. 4A is a side view of the first nail of the pedicle fixation system of FIG. 1.

FIG. 4B is a front view of the first nail of the pedicle fixation system of FIG. 1.

FIG. 4C is a side cross-sectional view of the first nail of the pedicle fixation system of FIG. 1.

DETAILED DESCRIPTION

As used herein, the term "proximal," when used in connection with a delivery device or components of a delivery device, refers to the end of the device closer to the user of the device when the device is being used as intended. On the other hand, the term "distal," when used in connection with a delivery device or components of a delivery device, refers to the end of the device farther away from the user when the device is being used as intended. As used herein, the terms "substantially," "generally," "approximately," and "about" are intended to mean that slight deviations from absolute are included within the scope of the term so modified.

Figure 1:
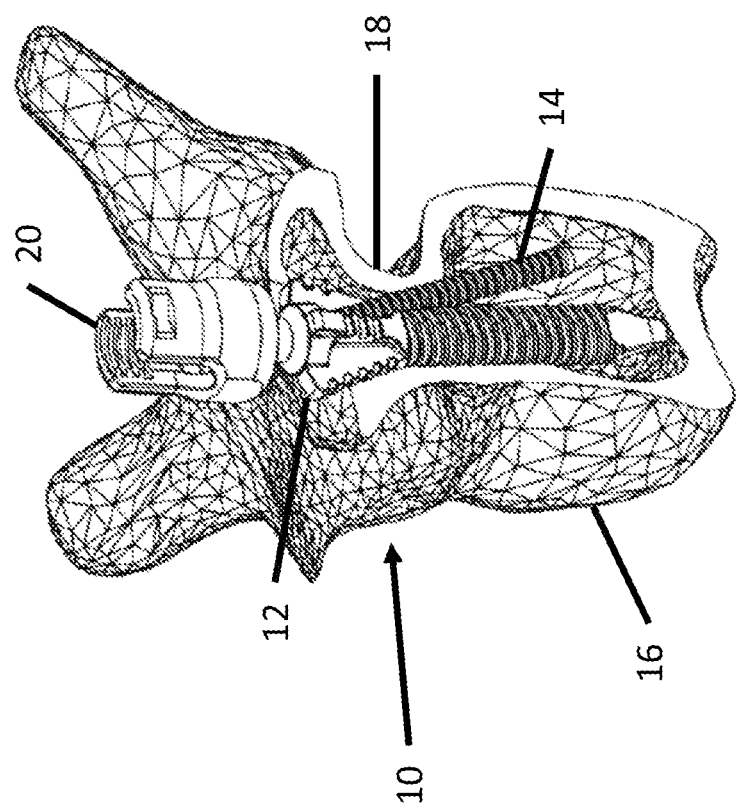
FIG. 1 is a perspective view of a vertebra with a pedicle fixation system attached thereto.

An exemplary pedicle fixation system 10 as may be used with various embodiments of the present disclosure is shown in a vertebra 16 in FIG. 1. Fixation system 10 includes a first nail 12 and a second nail 14 received through first nail 12. A coupling element 20 is pivotally coupled to first nail 12. Coupling element 20 may be, for example, any coupling element for coupling known pedicle screws to a spinal correction rod. For instance, coupling element 20 may be the same as any of the analogous elements disclosed in U.S. Pat. Nos. 6,488,681, 6,074,391, 6,261,287, 6,736,820, and 6,974,460, the disclosures of which are hereby incorporated by reference herein, or in any of the Xia, Radius, Denali, or Everest product lines offered by Stryker Corporation or its subsidiary, K2M, Inc. In the illustrated embodiment, coupling element 20 includes a generally spherical or hemispherical pocket for pivotally coupling to a head of first nail 12 and a U-shaped track for receiving a spinal correction rod. Coupling element 20 may be modular in design such that a distal opening to the pocket has an elastically deformable ring permitting coupling element 20 to snap-fit onto first head 22. In other embodiments, this modularity may be accomplished by any of the structures disclosed in U.S. Pat. Nos. 5,735,851, 5,800,435, 6,280,442, 7,947,065, 8,192,470, and 9,119,674, the disclosures of which are hereby incorporated by reference herein, or by any similar structures. The U-shaped track is internally threaded such that a set screw may ultimately act to retain the rod within the U-shaped track.

Both first nail 12 and second nail 14 are inserted in a pedicle 18 of vertebra 16. As such, second nail 12 is oriented in a direction that is generally anterior, but inclined caudally, toward the patient's feet. First nail 12 therefore enters pedicle 18 at a relatively superior location, and second nail enters pedicle 18 at a relatively inferior location. The orientation of first nail 12 and second nail 14 shown in FIG. 1 is largely dictated by anatomy, due to the relatively superior location of the pedicle to the vertebral body, but other orientations of first nail 12 and second nail 14 relative to pedicle 18 in other arrangements are also contemplated.

Figure 2:
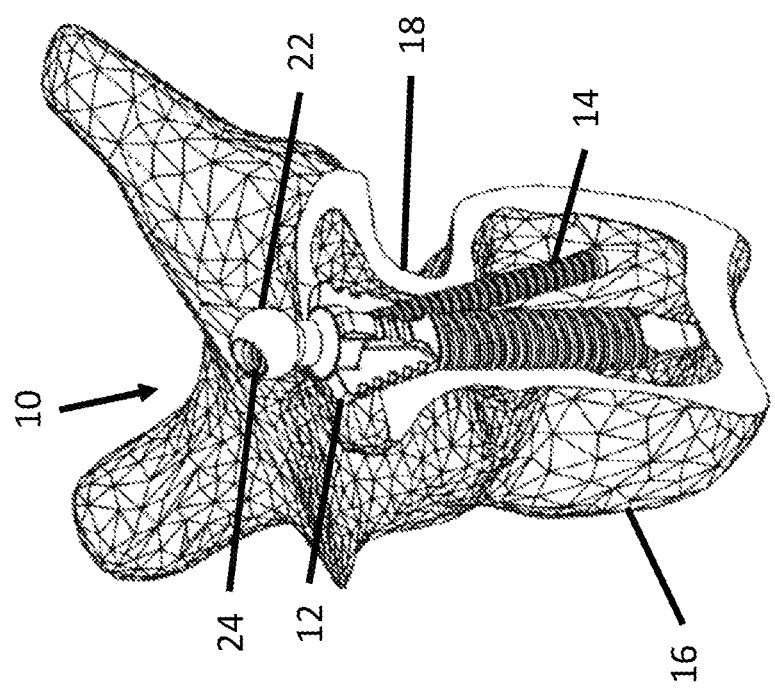
FIG. 2 illustrates the vertebra and pedicle fixation system of FIG. 1 without a coupling element.
Figure 3:
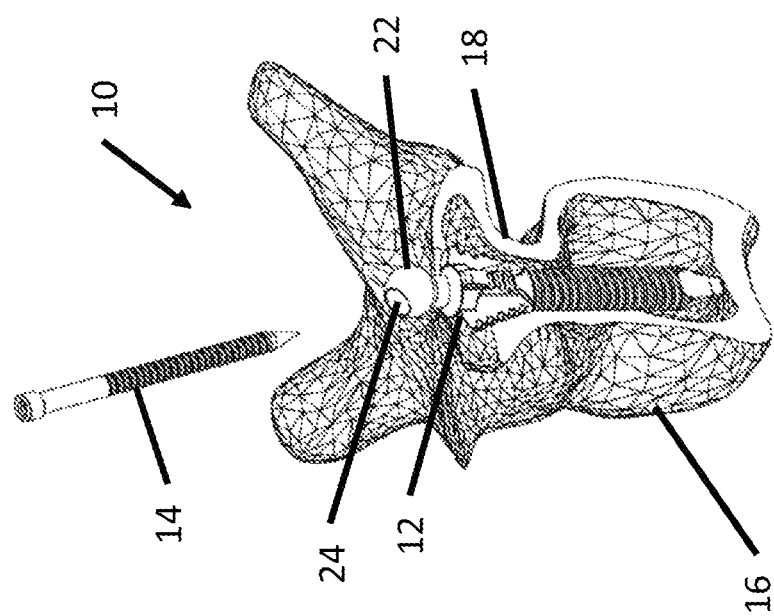
FIG. 3 illustrates the vertebra and pedicle fixation system of FIG. 2 with a first nail inserted in the vertebra and a second nail removed from the first nail.
Figure 4E:
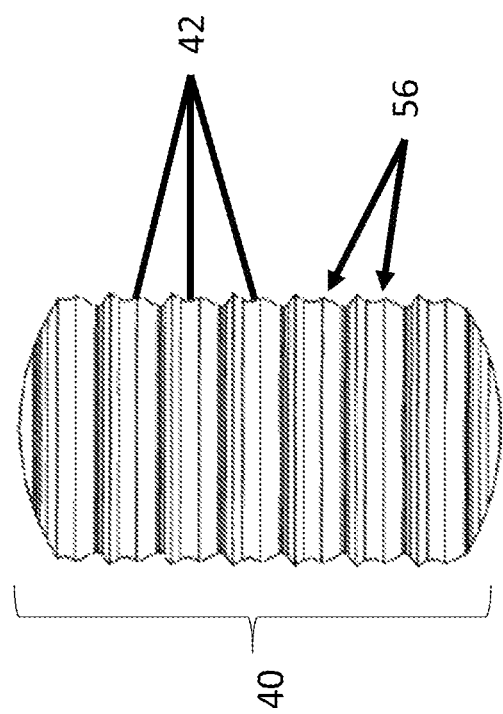
FIG. 4E is a close view of a portion of a shank of the first nail of the pedicle fixation system of FIG. 1.
Figure 4D:
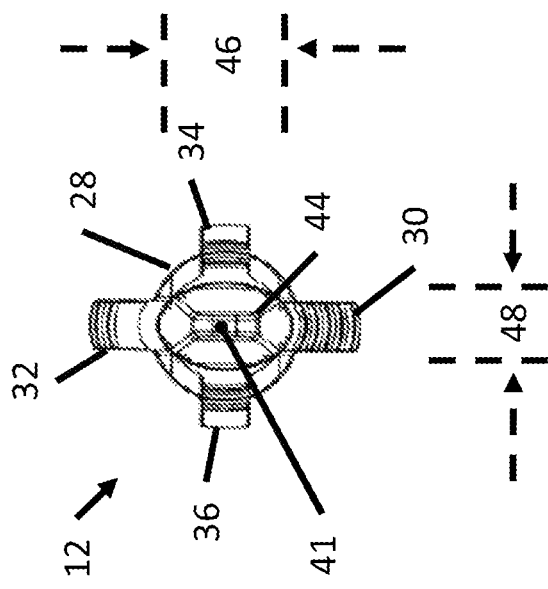
FIG. 4D is an end view of the first nail of the pedicle fixation system of FIG. 1.

FIGS. 2 and 3 illustrate pedicle fixation system 10 without coupling element 20 and with second nail 14 removed from first nail 12, respectively. As shown, first nail 12 has a spherical head 22 at a proximal end, and first head 22 includes an opening 24 through which second nail 14 is receivable.

FIGS. 4A-4E are detailed illustrations of the first nail 12, which includes a narrowed neck 26 that extends distally from first head 22 toward a platform 28. Neck 26 has a smaller diameter perpendicular to a first axis 41 than first head 22 and platform 28. A first shoulder 30, second shoulder 32, third shoulder 34, and fourth shoulder 36 extend radially from platform 28 relative to first axis 41. First and second shoulders 30, 32 are mutually opposite each other across first axis 41 and extend further from axis 41 than third and fourth shoulders 34, 36, which are also mutually opposite each other across axis 41. First and second shoulders 30, 32, are each perpendicular to both third shoulder 34 and fourth shoulder 36. Each shoulder 30, 32, 34, 36 includes radial notches 38 to facilitate engagement with pedicle 18.

Shoulders 30, 32, 34, 36 each taper distally and inward from their respective radially outermost points relative to first axis 41 to a first shank 40. First shank 40 extends distally along first axis 41 to first point 44. First shank 40 has a series of concentric rings 42 that define a textured surface 56 between shoulders 30, 32, 34, 36 and first point 44. Textured surface 56 provides resistance to axial movement of first nail 12 relative to bone after first nail 12 has been driven, thereby mitigating loosening of first nail 12 over time. First shank 40 also has a generally oval shaped cross section relative to first axis 41 defined by a width 46 defined perpendicular to first axis 41 and a thickness 48 defined perpendicular to both first axis 41 and width 46. Width 46 is greater than thickness 48. In some arrangements, for example, a ratio of width 46 to thickness 48 is at least 4:3.

Referring specifically to FIG. 4C, opening 24 communicates with a channel 52 that extends along a skew axis 51 to a groove 50 cut into second shoulder 32. Groove 50 is defined where channel 52 is not entirely circumferentially enclosed around skew axis 51 and where a generally cylindrical shape of channel 52 intersects with second shoulder 32 and first shank 40. Channel 52 includes a cavity 54 located at a proximal end or opening 24 of channel 52. Cavity 54 has a greater diameter perpendicular to skew axis 51 than channel 52. A difference between diameters of channel 52 and shelf 53 results in a generally radially extending surface or shelf 53 where channel 52 meets cavity 54.

Figure 5B:
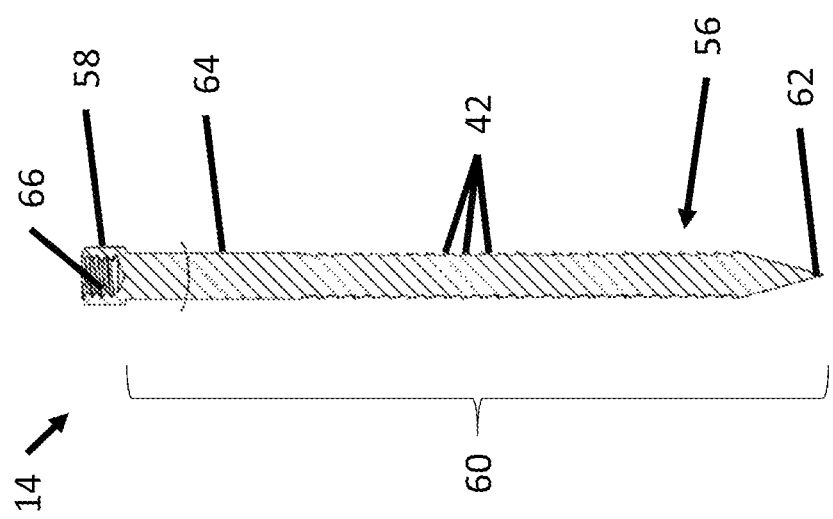
FIG. 5B is a side cross-sectional view of the second nail of the pedicle fixation system of FIG. 1.
Figure 5A:
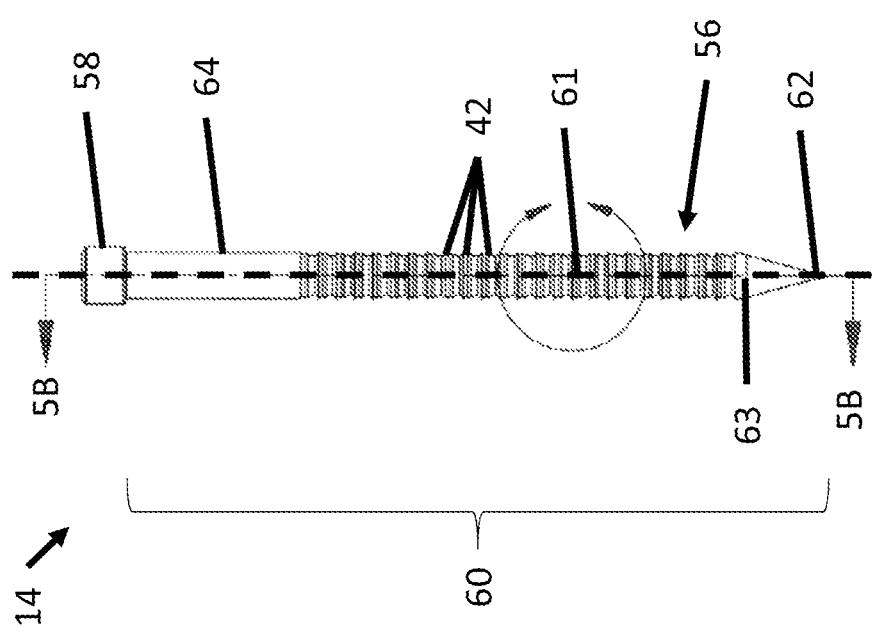
FIG. 5A is a side view of the second nail of the pedicle fixation system of FIG. 1.

Turning to FIGS. 5A and 5B, second nail 14 includes a second head 58 at a proximal end and a second shank 60 extending distally from second head 58 along second axis 63 to a point 62 at a distal end of the second nail 14. Similar to first shank 12, a portion of second shank 14 includes a textured surface 56 provided by a series of concentric rings 42 extending along the portion of second shank 14. However, second shank 60 further includes an untextured lag 64 between second head 58 and the portion of second shank 60 having textured surface 56. Lag 64 may have a length equal to or greater than a length of channel 52.

Second point 62, lag 64, and the portion of second shank 60 having textured surface 56 each have a diameter relative to second axis 63 that is equal to or less than the diameter of channel 52 perpendicular to skew axis 51. Second nail 14 is therefore receivable through channel 52. Similarly, second head 58 has a diameter perpendicular to second axis 63 that is equal to or less than the diameter of cavity 54 perpendicular to skew axis 51, so second head 58 is receivable within cavity 54. However, the diameter of second head 58 perpendicular to second axis 63 is greater than the diameter of channel 52 perpendicular to skew axis 51 except at cavity 54, or larger than an inner diameter of shelf 53 perpendicular to skew axis 51. As such, receipt of second head 58 within cavity 54 also results in second head 58 seating against shelf 53. Second head 58 also has internal threading 66 which may be used to anchor a retrieval device to second nail 14 for removing second nail 14 during a revision procedure or when pedicle fixation becomes unnecessary for the patient.

In alternative arrangements, the diameter of lag 64 or the portion of second shank 60 having textured surface 56 perpendicular to second axis 63 are slightly greater than the diameter of channel 52 relative to skew axis 51 to provide a slight interference fit between second nail 14 and channel 52. Similarly, in some arrangements the diameter of second head 58 relative to second axis 63 is slightly greater than the diameter of cavity 54 perpendicular to skew axis 51 to provide a slight interference fit between second head 58 and cavity 54.

Figure 6:
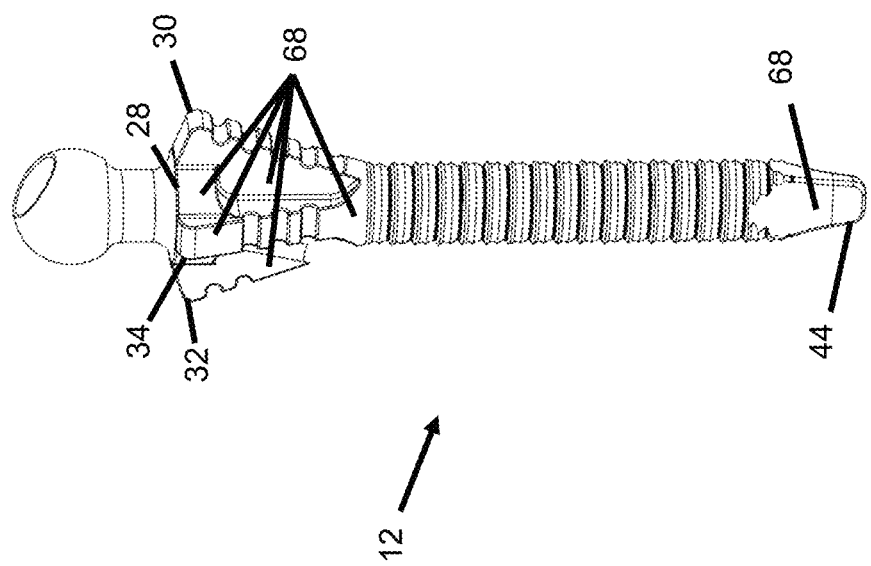
FIG. 6 is a side view of a first nail of another embodiment pedicle fixation system according to the present invention.

Fixation system 10 could be constructed of any suitable biocompatible material, such as stainless steel or titanium. Fixation system 10, particularly first nail 12 and second nail 14, may also be constructed partially or entirely from porous structures or materials, such as a porous metal. Such porous metal may be in the form of a porous, commercially-pure titanium matrix or a porous titanium alloy (e.g., a TI6Al4V alloy), such as those manufactured by Howmedica Osteonics Corp. under the trademark TRITANIUM®. In some examples, such alloys or porous structures are constructed with additive layer manufacturing, such as selective laser sintering, selective laser melting, and electron beam melting. Examples of additive manufacturing processes for creating some or all of the components of the system 10 disclosed herein, including some such processes for creating porous materials, are disclosed in U.S. Pat. Nos. 7,537,664, 8,147,861, 8,350,186, 8,728,387, 8,992,703, 9,135,374, 9,180,010, and 9,456,901 as well as U.S. Patent Application Publication No. 2006/0147332, all of which are hereby incorporated by reference. Some arrangements include porous material or Tritanium on flat surfaces, particularly flat surfaces that are generally radially oriented, of first nail 12. By way of example, FIG. 6 shows an arrangement of first nail 14 with Tritanium surfaces 68 on platform 28, shoulders 30, 32, 34, 36 (fourth shoulder 36 not shown), and first point 44.

Pedicle fixation system 10 enables a method of fixing a spinal correction rod to the patient's spine that may be faster, more efficient, and have improved resistance to drifting and loosening than certain known spinal correction methods. In an exemplary method, first nail 12 is driven into pedicle 18 in a first direction that is perpendicular to a surface of pedicle 18, or generally anterior relative to the patient such that first axis 41 is aligned with the first direction. First nail is driven into pedicle 18 such that some of notches 38 are aligned with the periosteum or cortical bone of pedicle 18. A physician driving first nail 12 into pedicle 18 may use notches 38 and platform 28 to estimate a depth of first nail 12 and determine when first nail 12 has been driven an appropriate distance into pedicle 18. First nail 12 is oriented relative to pedicle 18 such that first shoulder 30 and second shoulder 32 both extend generally neuraxially. Shoulders 30, 32, 34, 36 and notches 38 both prevent rotation of first nail 12 relative to pedicle 18, thereby preventing loosening of first nail 12. Width 46 and the relatively long first shoulder 30 and second shoulder 32 are therefore aligned with a longer dimension of pedicle 18 than thickness 48 and the relatively short third shoulder 34 and fourth shoulder 36. In particular, second shoulder 32 is oriented caudally, toward the patient's feet. Skew axis 51, which extends from opening 24 radially relative to first axis 41 in the same direction as second shoulder 32 is therefore transverse to first axis 41 such that skew axis 51 has a greater neuraxial component than first axis 41.

Second nail 14 is then driven into pedicle 18 through channel 52 such that second axis 63 is aligned with skew axis 51 and second head 58 is seated within cavity 54 against shelf 53. Second nail 14 thereby acts to secondarily fasten first nail 12 to pedicle 18, preventing loosening or drifting of first nail 12 relative to pedicle 18. The driving of first nail 12 and second nail 14 may be accomplished with a hammer such as, for example, an electric or pneumatic impact hammer. Use of a hammer, particularly an impact hammer, may allow implant of several fixation systems 10 with less time and effort, and consequently less fatigue to the operating physician, than known fixation systems, which typically include pedicle screws.

After first nail 12 and second nail 14 are driven into pedicle 18, coupling element 20 is pivotally coupled to first head 22. Upon fixation of an intended number of fixation systems 10 and coupling of respective coupling elements 20, a spinal correction rod may be positioned near coupling elements 20 and reduced onto fixation systems 10 according to known methods. The rod may then be connected to coupling elements 20 with set screws engaged with the threads of coupling elements 20, as in standard pedicle screw operations.

Figure 7:
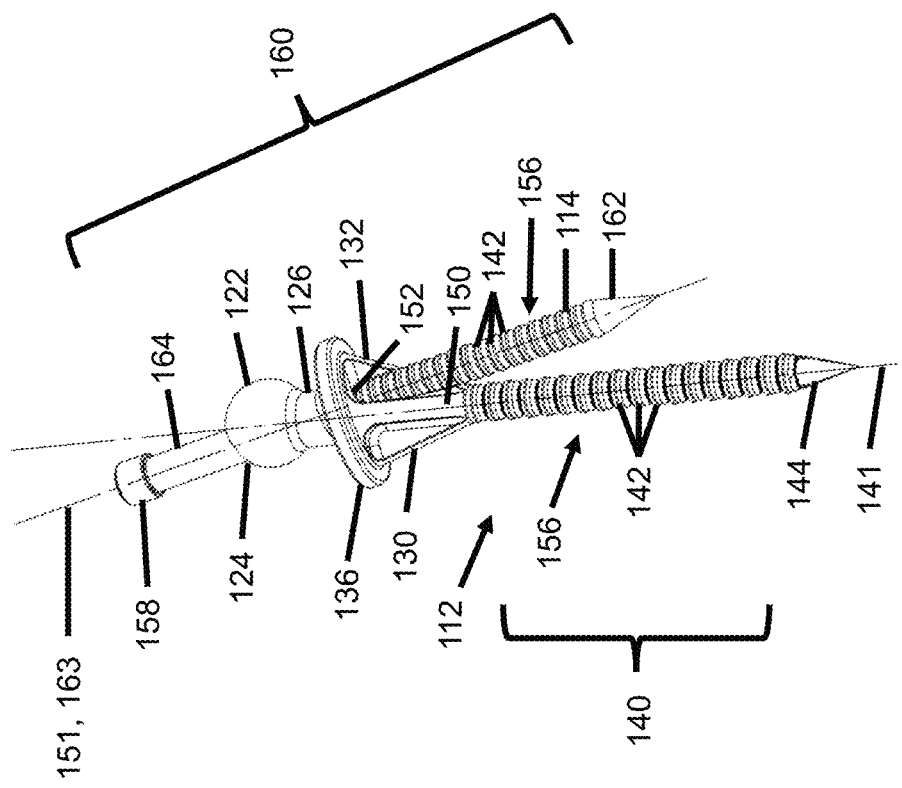
FIG. 7 is a side view of another arrangement of the pedicle fixation system according to the present invention.

FIG. 7 illustrates a fixation system 110 according to another embodiment, with like numerals generally referring to like features, but within the 100-series of numerals (i.e., element 122 is a first head of the embodiment of FIG. 7 similar to first head 22 of the embodiment described above). As such, repeated description of certain common aspects of the embodiments are omitted below.

First nail 112 includes a platform 136 extending perpendicularly to skew axis 163. Platform 136 thereby matches a natural angle of the lamina corresponding to pedicle 18 and functions to limit a depth to which first nail 11 can be driven into pedicle 18. Further, platform 136 is circular and centered about skew axis 151. A radially outermost point of first nail 112 relative to first axis 141 in any given direction is also a radially outermost point of platform 136 relative to skew axis 151 in the given direction.

First shoulder 130 and second shoulder 132 extend from a distal side of platform 136 and taper radially inward relative to first axis 141 and distally toward first shank 140. First shank 140 is circular in axial cross section. Second shoulder 132 includes groove 150 and extends from a most proximal circumferential position of platform 136.

First nail 112 and second nail 114 may be made from any of the materials described above with regard to the embodiment of FIGS. 1-6. For example, first nail 112 and second nail 114 may be constructed of any sufficiently strong biocompatible material, such as titanium or nitinol. Either or both of first nail 112 and second nail 114 may include porous structures to promote bone in-growth, such as Tritanium.

A method for fixing a spinal fixation rod using first nail 112 and second nail 114 is generally similar to the method described above with regard to the embodiment of FIGS. 1-6. First nail 112 is driven into a pedicle, such as pedicle 18, in a first direction that is generally anterior relative to a patient. Second nail 114 is driven through a channel 152 and into pedicle 18 in a second direction. The second direction is generally anterior, but has a greater neuraxial component than the first direction. For example, the second direction may be tilted caudally toward the patient's feet relative to the first direction. Driving either or both of first nail 112 and second nail 114 is accomplished by hammering, such as with an impact hammer. After first nail 112 and second nail 114 are driven, coupling element 20 is pivotally coupled to first head 122. The patient's spine is then manipulated to an intended alignment and the spinal fixation rod is reduced onto coupling element 20. The spinal fixation rod is finally set onto coupling element 20 with a set screw.

Certain modifications or variations on the examples described above are contemplated within the scope of this disclosure. For example, axial cross sections of first nail 12, 112 and second nail 14, 114 could differ from those depicted in FIGS. 1-7, such as by having generally polygonal geometry. For example, either or both of first shank 40, 140 and second shank 60, 160 may have square or quadrilateral axial cross sectional shapes. Channel 52, 152 may have any axial cross sectional shape relative to skew axis 51, 151 to match the cross sectional shape of second shank 60, 160. Second head 58, 158 and cavity 54 (present but not illustrated in first nail 112) may similarly have a polygonal axial cross section relative to second axis 63, 163 and skew axis 51, 151. The density, shape, and size of notches 38 and rings 42 may also differ from those depicted in FIGS. 1-7. First nail 12, 112 may additionally have more or fewer shoulders 30, 32, 34, 36, 130, 132.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pedicle fixation system, comprising:
   a first fastener, the first fastener including a first head at a proximal end, a first shank extending distally from the first head along a first fastener axis and a channel extending along a skew axis, the skew axis being transverse to the first axis and the channel having a channel diameter perpendicular to the skew axis, wherein the channel extends into a shoulder spaced apart from the head, said shoulder extending radially outwards from the first fastener relative to the first axis; and
   a second fastener extending through the channel, the second fastener including a second shank extending along a second fastener axis, at least a distal part of the second shank having a second fastener diameter perpendicular to the second fastener axis, the second fastener diameter being smaller than the channel diameter.

2. The pedicle fixation system of claim 1, wherein the first fastener includes a generally spherical first head.

3. The pedicle fixation system of claim 2, wherein the channel extends from an opening in the first head.

4. The pedicle fixation system of claim 2, comprising a coupling element that includes a pocket shaped to pivotally couple to the first head.

5. The fastener of claim 4, wherein the coupling element includes a track shaped to couple to a rod.

6. The pedicle fixation system of claim 1, wherein a majority of the first shank has a generally oval shaped axial cross section relative to the first fastener axis.

7. The pedicle fixation system of claim 6, wherein the generally oval shaped cross section has a width to thickness ratio of at least 4:3.

8. The pedicle fixation system of claim 1, wherein:
   the first fastener includes a cavity at a proximal end of the channel and a shelf located between the cavity and the channel; and
   the second fastener includes a second head having a second head diameter that is greater than an inner diameter of the shelf.

9. The pedicle fixation system of claim 1, wherein the first fastener comprises:
   a platform between the first head and the first shank that extends in a radial direction perpendicular to the first axis; and
   a neck between the first head and the platform, the neck having a smaller radius perpendicular to the first axis than the first head and the platform.

10. The pedicle fixation system of claim 9, wherein the first fastener includes at least one shoulder that extends to a radially outermost point distal of the neck and tapers radially inward from the radially outermost point to the first shank.

11. The pedicle fixation system of claim 10, wherein the at least one shoulder includes a series of notches on a radially outer surface.

12. The fastener of claim 1, wherein the first fastener is a first nail.

13. The fastener of claim 12, wherein the second fastener is a second nail.

14. A method installing a pedicle fixation system, comprising:
   inserting a first fastener into a vertebral body in a first direction; and
   inserting a second fastener in a second direction transverse to the first direction through a channel of the first fastener and into the vertebral body such that the second fastener secondarily fastens the first fastener to the vertebral body, wherein a head of the second fastener is seated within a cavity at a proximal end of the channel and a planar surface is located between the cavity and the channel.

15. The method of claim 14, wherein the step of inserting the first fastener includes hammering the first fastener into the vertebral body.

16. The method of claim 14, wherein the step of inserting the second fastener includes hammering the second fastener into the vertebral body.

17. The method of claim 14, comprising:
   hammering a third fastener into a second vertebral body;
   attaching coupling elements to the first and third fasteners; and
   inserting a rod through the coupling elements such that the first and third fasteners are coupled to the rod.

* * * * *